US011083519B2

(12) United States Patent
Rioux et al.

(10) Patent No.: US 11,083,519 B2
(45) Date of Patent: *Aug. 10, 2021

(54) TREATMENT DEVICES AND METHODS

(71) Applicant: Innoblative Designs, Inc., Chicago, IL (US)

(72) Inventors: Robert F. Rioux, Ashland, MA (US); Michelle Hasse, Eau Claire, MI (US); Tyler Wanke, Chicago, IL (US)

(73) Assignee: Innoblative Designs, Inc., Chicago, IL (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/592,020

(22) Filed: Oct. 3, 2019

(65) Prior Publication Data

US 2020/0030026 A1      Jan. 30, 2020

Related U.S. Application Data

(63) Continuation of application No. 16/122,111, filed on Sep. 5, 2018, now Pat. No. 10,470,818, which is a (Continued)

(51) Int. Cl.
*A61B 18/14* (2006.01)
*A61B 18/00* (2006.01)
(Continued)

(52) U.S. Cl.
CPC ........ *A61B 18/1492* (2013.01); *A61B 18/148* (2013.01); *A61B 5/01* (2013.01);
(Continued)

(58) Field of Classification Search
CPC ........... A61B 2018/00005; A61B 2018/00011; A61B 2018/00065; A61B 2018/0016;
(Continued)

(56) References Cited

U.S. PATENT DOCUMENTS 4,699,147 A    10/1987  Chilson et al.
4,976,711 A    12/1990  Parins et al.
(Continued)

FOREIGN PATENT DOCUMENTS

CN        2610858 Y     4/2004
CN      104546124 A     4/2015
(Continued)

OTHER PUBLICATIONS

Extended European Search Report dated Jun. 10, 2016 for European Application No. 13825361.2 (13 Pages).
(Continued)

*Primary Examiner* — Michael F Peffley
(74) *Attorney, Agent, or Firm* — Brown Rudnick LLP

(57)  ABSTRACT

The present invention is directed to a medical device for providing treatment to diseased tissue and cells. The medical device is configured to ablate a target tissue surface, optionally within a resection cavity, and further deliver a therapeutic that targets diseased (e.g., cancer) cells via a marker whose expression is upregulated by the ablation. The ablation directly kills diseased cells associated with the tissue surface. While some diseased cells evade direct ablation, those cells nevertheless upregulate certain cell surface markers in response to the ablation, even while other, healthy or normal cells do not upregulate expression of the marker in response to the ablation. Devices and methods disclosed herein are used to deliver a therapeutic that uses the upregulated cell surface marker to cause the death of those diseased cells.

18 Claims, 7 Drawing Sheets

Related U.S. Application Data continuation of application No. 15/784,778, filed on Oct. 16, 2017, now Pat. No. 10,070,921.

(60) Provisional application No. 62/409,103, filed on Oct. 17, 2016.

(51) Int. Cl.
  *A61B 5/0538* (2021.01)
  *A61B 5/01* (2006.01)
  *A61B 5/287* (2021.01)

(52) U.S. Cl.
  CPC ............. *A61B 5/0538* (2013.01); *A61B 5/287* (2021.01); *A61B 18/14* (2013.01); *A61B 2018/00005* (2013.01); *A61B 2018/00011* (2013.01); *A61B 2018/0016* (2013.01); *A61B 2018/00255* (2013.01); *A61B 2018/00333* (2013.01); *A61B 2018/00577* (2013.01); *A61B 2018/00904* (2013.01); *A61B 2018/144* (2013.01); *A61B 2018/1405* (2013.01); *A61B 2018/1467* (2013.01); *A61B 2018/1472* (2013.01); *A61B 2218/002* (2013.01); *H05K 999/99* (2013.01)

(58) Field of Classification Search
  CPC .. A61B 2018/00214; A61B 2018/0022; A61B 2018/00238; A61B 2018/00255; A61B 2018/00333; A61B 2018/00577; A61B 2018/1405; A61B 2018/144; A61B 2018/1467; A61B 2018/1472; A61B 18/14; A61B 18/148; A61B 18/1492; A61B 2218/002

See application file for complete search history.

(56) References Cited

U.S. PATENT DOCUMENTS

| | | |
|---|---|---|
| 4,979,948 A | 12/1990 | Geddes et al. |
| 5,045,056 A | 9/1991 | Behl |
| 5,100,423 A | 3/1992 | Fearnot |
| 5,117,828 A | 6/1992 | Metzger et al. |
| 5,163,938 A | 11/1992 | Kambara et al. |
| 5,334,193 A | 8/1994 | Nardella |
| 5,429,605 A | 7/1995 | Richling et al. |
| 5,471,982 A | 12/1995 | Edwards et al. |
| 5,472,441 A | 12/1995 | Edwards et al. |
| 5,486,161 A | 1/1996 | Lax et al. |
| 5,536,267 A | 7/1996 | Edwards et al. |
| 5,562,720 A | 10/1996 | Stern et al. |
| 5,657,760 A | 8/1997 | Ying et al. |
| 5,672,153 A | 9/1997 | Lax et al. |
| 5,672,173 A | 9/1997 | Gough et al. |
| 5,672,174 A | 9/1997 | Gough et al. |
| 5,683,384 A | 11/1997 | Gough et al. |
| 5,713,942 A | 2/1998 | Stern et al. |
| 5,728,143 A | 3/1998 | Gough et al. |
| 5,772,590 A | 6/1998 | Webster, Jr. |
| 5,782,827 A | 7/1998 | Gough et al. |
| 5,827,276 A | 10/1998 | LeVeen et al. |
| 5,840,076 A | 11/1998 | Swanson et al. |
| 5,846,239 A | 12/1998 | Swanson et al. |
| 5,855,576 A | 1/1999 | LeVeen et al. |
| 5,863,290 A | 1/1999 | Gough et al. |
| 5,868,736 A | 2/1999 | Swanson et al. |
| 5,868,776 A | 2/1999 | Wright |
| 5,871,483 A | 2/1999 | Jackson et al. |
| 5,888,198 A | 3/1999 | Eggers et al. |
| 5,891,136 A | 4/1999 | McGee et al. |
| 5,893,847 A | 4/1999 | Kordis |
| 5,913,855 A | 6/1999 | Gough et al. |
| 5,928,229 A | 7/1999 | Gough et al. |
| 5,935,123 A | 8/1999 | Edwards et al. |
| 5,961,513 A | 10/1999 | Swanson et al. |
| 5,980,517 A | 11/1999 | Gough |
| 6,009,877 A | 1/2000 | Edwards |
| 6,032,077 A | 2/2000 | Pomeranz |
| 6,036,689 A | 3/2000 | Tu et al. |
| 6,053,913 A | 4/2000 | Tu et al. |
| 6,053,937 A | 4/2000 | Edwards et al. |
| 6,063,081 A | 5/2000 | Mulier et al. |
| 6,071,278 A | 6/2000 | Panescu et al. |
| 6,071,280 A | 6/2000 | Edwards et al. |
| 6,099,526 A | 8/2000 | Whayne et al. |
| 6,112,123 A | 8/2000 | Kelleher et al. |
| 6,123,718 A | 9/2000 | Tu et al. |
| 6,142,993 A | 11/2000 | Whayne et al. |
| 6,221,071 B1 | 4/2001 | Sherry et al. |
| 6,241,666 B1 | 6/2001 | Pomeranz et al. |
| 6,251,109 B1 | 6/2001 | Hassett et al. |
| 6,258,087 B1 | 7/2001 | Edwards et al. |
| 6,309,352 B1 | 10/2001 | Oraevsky et al. |
| 6,312,408 B1 | 11/2001 | Eggers et al. |
| 6,312,429 B1 | 11/2001 | Burbank et al. |
| 6,358,248 B1 | 3/2002 | Mulier et al. |
| 6,379,353 B1 | 4/2002 | Nichols |
| 6,409,722 B1 | 6/2002 | Hoey et al. |
| 6,425,877 B1 | 7/2002 | Edwards |
| 6,454,766 B1 | 9/2002 | Swanson et al. |
| 6,475,213 B1 | 11/2002 | Whayne et al. |
| 6,491,710 B2 | 12/2002 | Satake |
| 6,494,902 B2 | 12/2002 | Hoey et al. |
| 6,503,247 B2 | 1/2003 | Swartz et al. |
| 6,522,930 B1 | 2/2003 | Schaer et al. |
| 6,537,248 B2 | 3/2003 | Mulier et al. |
| 6,537,272 B2 | 3/2003 | Christopherson et al. |
| 6,544,262 B2 | 4/2003 | Fleischman |
| 6,551,310 B1 | 4/2003 | Ganz et al. |
| 6,585,732 B2 | 7/2003 | Mulier et al. |
| 6,623,481 B1 | 9/2003 | Garbagnati et al. |
| 6,638,275 B1 | 10/2003 | McGaffigan et al. |
| 6,648,883 B2 | 11/2003 | Francischelli et al. |
| 6,663,622 B1 | 12/2003 | Foley et al. |
| 6,692,466 B1 | 2/2004 | Chow et al. |
| 6,736,810 B2 | 5/2004 | Hoey et al. |
| 6,736,811 B2 | 5/2004 | Panescu et al. |
| 6,743,226 B2 | 6/2004 | Cosman et al. |
| 6,764,487 B2 | 7/2004 | Mulier et al. |
| 6,770,072 B1 | 8/2004 | Truckai et al. |
| 6,780,183 B2 | 8/2004 | Jimenez, Jr. et al. |
| 6,805,131 B2 | 10/2004 | Kordis |
| 6,826,421 B1 | 11/2004 | Beatty et al. |
| 6,849,073 B2 | 2/2005 | Hoey et al. |
| 6,872,206 B2 | 3/2005 | Edwards et al. |
| 6,878,149 B2 | 4/2005 | Gatto |
| 6,955,641 B2 | 10/2005 | Lubock |
| 6,978,788 B2 | 12/2005 | Klimberg et al. |
| 6,984,232 B2 | 1/2006 | Vanney et al. |
| 7,104,989 B2 | 9/2006 | Skarda |
| 7,150,745 B2 | 12/2006 | Stern et al. |
| 7,156,845 B2 | 1/2007 | Mulier et al. |
| 7,169,144 B2 | 1/2007 | Hoey et al. |
| 7,247,155 B2 | 7/2007 | Hoey et al. |
| 7,276,061 B2 | 10/2007 | Schaer et al. |
| 7,306,593 B2 | 12/2007 | Keidar et al. |
| 7,311,708 B2 | 12/2007 | McClurken |
| 7,326,208 B2 | 2/2008 | Vanney et al. |
| 7,344,535 B2 | 3/2008 | Stern et al. |
| 7,364,579 B2 | 4/2008 | Mulier et al. |
| 7,367,972 B2 | 5/2008 | Francischelli et al. |
| 7,371,231 B2 | 5/2008 | Rioux et al. |
| 7,399,299 B2 | 7/2008 | Daniel et al. |
| 7,416,552 B2 | 8/2008 | Paul et al. |
| 7,419,489 B2 | 9/2008 | Vanney et al. |
| 7,507,234 B2 | 3/2009 | Utley et al. |
| 7,507,238 B2 | 3/2009 | Edwards et al. |
| 7,530,979 B2 | 5/2009 | Ganz et al. |
| 7,556,628 B2 | 7/2009 | Utley et al. |
| 7,632,268 B2 | 12/2009 | Edwards et al. |
| 7,717,909 B2 | 5/2010 | Strul et al. |
| 7,769,432 B2 | 8/2010 | Klimberg et al. |
| 7,776,034 B2 | 8/2010 | Kampa |

(56) References Cited

U.S. PATENT DOCUMENTS

| | | |
|---|---|---|
| 7,828,793 B2 | 11/2010 | Thompson et al. |
| 7,862,498 B2 | 1/2011 | Nguyen et al. |
| 7,879,030 B2 | 2/2011 | Paul et al. |
| 7,942,873 B2 | 5/2011 | Kwan et al. |
| 7,959,627 B2 | 6/2011 | Utley et al. |
| 7,959,628 B2 | 6/2011 | Schaer et al. |
| 7,959,631 B2 | 6/2011 | DiCarlo |
| 7,993,336 B2 | 8/2011 | Jackson et al. |
| 7,997,278 B2 | 8/2011 | Utley et al. |
| 8,012,149 B2 | 9/2011 | Jackson et al. |
| 8,034,022 B2 | 10/2011 | Boatman |
| 8,043,289 B2 | 10/2011 | Behl et al. |
| 8,048,069 B2 | 11/2011 | Skwarek et al. |
| 8,114,071 B2 | 2/2012 | Woloszko et al. |
| 8,224,416 B2 | 7/2012 | de la Rama et al. |
| 8,303,584 B2 | 11/2012 | Burdio Pinilla et al. |
| 8,388,573 B1 | 3/2013 | Cox |
| 8,398,624 B2 | 3/2013 | Rioux et al. |
| 8,409,193 B2 | 4/2013 | Young et al. |
| 8,444,638 B2 | 5/2013 | Woloszko et al. |
| 8,465,484 B2 | 6/2013 | Davalos et al. |
| 8,465,486 B2 | 6/2013 | Danek et al. |
| 8,518,018 B2 | 8/2013 | Minskoff et al. |
| 8,588,886 B2 | 11/2013 | de la Rama et al. |
| 8,591,461 B2 | 11/2013 | Boatman |
| 8,617,158 B2 | 12/2013 | Garabedian et al. |
| 8,647,339 B2 | 2/2014 | Satake |
| 8,657,814 B2 | 2/2014 | Werneth et al. |
| 8,734,439 B2 | 5/2014 | Gough et al. |
| 8,814,855 B2 | 8/2014 | DiCarlo et al. |
| 8,834,461 B2 | 9/2014 | Werneth et al. |
| 8,979,838 B2 | 3/2015 | Woloszko et al. |
| 8,979,841 B2 | 3/2015 | Kunis et al. |
| 9,078,665 B2 | 7/2015 | Moss et al. |
| 9,131,980 B2 | 9/2015 | Bloom |
| 9,839,472 B2 | 12/2017 | Rioux et al. |
| 9,848,936 B2 | 12/2017 | Rioux et al. |
| 9,855,098 B2 | 1/2018 | Rioux |
| 2001/0031941 A1 | 10/2001 | Edwards et al. |
| 2002/0026186 A1 | 2/2002 | Woloszko et al. |
| 2002/0062123 A1 | 5/2002 | McClurken et al. |
| 2002/0087208 A1 | 7/2002 | Koblish et al. |
| 2002/0095152 A1 | 7/2002 | Ciarrocca et al. |
| 2002/0115992 A1 | 8/2002 | Utley et al. |
| 2002/0120259 A1 | 8/2002 | Lettice et al. |
| 2002/0120267 A1 | 8/2002 | Phan |
| 2002/0128641 A1 | 9/2002 | Underwood et al. |
| 2003/0009166 A1 | 1/2003 | Moutafis et al. |
| 2003/0036680 A1 | 2/2003 | Black |
| 2003/0130711 A1 | 7/2003 | Pearson et al. |
| 2003/0216725 A1 | 11/2003 | Woloszko et al. |
| 2003/0225403 A1 | 12/2003 | Woloszko et al. |
| 2004/0087936 A1 | 5/2004 | Stern et al. |
| 2004/0092960 A1 | 5/2004 | Abrams et al. |
| 2005/0049454 A1 | 3/2005 | Ouchi |
| 2005/0070894 A1 | 3/2005 | McClurken |
| 2005/0154386 A1 | 7/2005 | West et al. |
| 2005/0187491 A1 | 8/2005 | Burbank et al. |
| 2006/0069385 A1 | 3/2006 | Lafontaine et al. |
| 2006/0212032 A1 | 9/2006 | Daniel et al. |
| 2006/0259027 A1 | 11/2006 | Kwan et al. |
| 2007/0083195 A1 | 4/2007 | Werneth et al. |
| 2008/0004534 A1 | 1/2008 | Gelbart et al. |
| 2008/0015565 A1 | 1/2008 | Davison |
| 2008/0103494 A1 | 5/2008 | Rioux et al. |
| 2008/0140001 A1 | 6/2008 | Globerman et al. |
| 2008/0234673 A1 | 9/2008 | Marion et al. |
| 2009/0171340 A1 | 7/2009 | Young |
| 2009/0177193 A1 | 7/2009 | Wang et al. |
| 2009/0248021 A1 | 10/2009 | McKenna |
| 2009/0292177 A1 | 11/2009 | Eggers et al. |
| 2009/0299355 A1 | 12/2009 | Bencini et al. |
| 2010/0114087 A1 | 5/2010 | Edwards et al. |
| 2010/0256629 A1 | 10/2010 | Wylie et al. |
| 2010/0292689 A1 | 11/2010 | Davison et al. |
| 2011/0172485 A1 | 7/2011 | Lubock |
| 2011/0257646 A1 | 10/2011 | Utley et al. |
| 2012/0029510 A1 | 2/2012 | Haverkost |
| 2012/0059437 A1 | 3/2012 | Shalev |
| 2012/0109250 A1 | 5/2012 | Cates et al. |
| 2012/0172680 A1 | 7/2012 | Gelfand et al. |
| 2013/0085493 A1 | 4/2013 | Bloom et al. |
| 2013/0131649 A1 | 5/2013 | Hughett, Sr. et al. |
| 2013/0158536 A1 | 6/2013 | Bloom |
| 2013/0172870 A1 | 7/2013 | Germain et al. |
| 2013/0184702 A1 | 7/2013 | Neal, II et al. |
| 2013/0184706 A1 | 7/2013 | Gelbart et al. |
| 2013/0253506 A1 | 9/2013 | Rioux et al. |
| 2013/0310833 A1 | 11/2013 | Brown et al. |
| 2013/0338662 A1 | 12/2013 | Weber |
| 2014/0018788 A1 | 1/2014 | Engelman et al. |
| 2014/0018794 A1 | 1/2014 | Anderson et al. |
| 2014/0031810 A1 | 1/2014 | Mahvi et al. |
| 2014/0058376 A1 | 2/2014 | Horn et al. |
| 2014/0180273 A1 | 6/2014 | Nair |
| 2014/0221998 A1 | 8/2014 | Latterell |
| 2014/0276731 A1 | 9/2014 | Voegele et al. |
| 2014/0276748 A1 | 9/2014 | Ku et al. |
| 2014/0296842 A1 | 10/2014 | Mansi et al. |
| 2014/0378960 A1 | 12/2014 | Fischer et al. |
| 2015/0018817 A1 | 1/2015 | Willard |
| 2015/0141982 A1 | 5/2015 | Lee |
| 2015/0306361 A1 | 10/2015 | Feig et al. |
| 2016/0015444 A1 | 1/2016 | Wittenberger |
| 2016/0045197 A1 | 2/2016 | Mitelberg et al. |
| 2016/0113707 A1 | 4/2016 | Sahakian et al. |
| 2016/0113708 A1 | 4/2016 | Moss et al. |
| 2016/0184008 A1 | 6/2016 | Papaioannou et al. |
| 2016/0317221 A1 | 11/2016 | Rioux |
| 2017/0000559 A1 | 1/2017 | Rioux et al. |
| 2017/0027633 A1 | 2/2017 | Wham et al. |
| 2017/0119454 A1 | 5/2017 | Rioux et al. |
| 2017/0172646 A1 | 6/2017 | Patel et al. |
| 2017/0215947 A1 | 8/2017 | Rioux et al. |
| 2017/0215951 A1 | 8/2017 | Wang et al. |
| 2017/0252092 A1 | 9/2017 | Rioux et al. |
| 2017/0281267 A1 | 10/2017 | Rioux et al. |
| 2017/0281271 A1 | 10/2017 | Rioux |
| 2018/0014880 A1 | 1/2018 | Rioux et al. |
| 2018/0078305 A1 | 3/2018 | Rioux et al. |
| 2018/0104004 A1 | 4/2018 | Rioux et al. |

FOREIGN PATENT DOCUMENTS

| | | |
|---|---|---|
| DE | 102010032932 A1 | 2/2012 |
| EP | 0777445 B1 | 6/1999 |
| EP | 2942023 A3 | 2/2016 |
| EP | 3040043 B1 | 1/2018 |
| JP | 3009735 B2 | 2/2000 |
| JP | 2010-505596 A | 2/2010 |
| JP | 2010-155083 A | 7/2010 |
| JP | 2013-532552 A | 8/2013 |
| JP | 2015-100706 A | 6/2015 |
| JP | 2016-127919 A | 7/2016 |
| WO | 9510326 A1 | 4/1995 |
| WO | 9942047 A1 | 8/1999 |
| WO | 0051683 A1 | 9/2000 |
| WO | 01/74252 A2 | 10/2001 |
| WO | 2007103986 A2 | 9/2007 |
| WO | 2011143468 A2 | 11/2011 |
| WO | 2012015722 A1 | 2/2012 |
| WO | 2012050637 A1 | 4/2012 |
| WO | 2013134733 A3 | 11/2013 |
| WO | 2014022379 A1 | 2/2014 |
| WO | 2014189887 A2 | 11/2014 |
| WO | 2015/142674 A1 | 9/2015 |
| WO | 2015163846 A1 | 10/2015 |
| WO | 2015200518 A1 | 12/2015 |
| WO | 2016/176567 A1 | 11/2016 |
| WO | 2016/181316 A1 | 11/2016 |

(56) References Cited

FOREIGN PATENT DOCUMENTS

| | | |
|---|---|---|
| WO | 2016181318 A1 | 11/2016 |
| WO | 2019023328 A1 | 1/2019 |

OTHER PUBLICATIONS

International Search Report and Written Opinion of the International Searching Authority dated Aug. 22, 2016 for International Application No. PCT/US2016/030081 (11 Pages).

International Search Report and Written Opinion of the International Searching Authority dated Aug. 5, 2015 for International Application No. PCT/US2015/020596 (13 Pages).

International Search Report and Written Opinion of the International Searching Authority dated Feb. 2, 2017 for International Application No. PCT/US2016/059345 (10 Pages).

International Search Report and Written Opinion of the International Searching Authority dated May 16, 2017 for International Application No. PCT/US2017/015582 (11 pages).

International Search Report and Written Opinion of the International Searching Authority dated Nov. 29, 2013 for International Application No. PCT/US2013/052703 (11 Pages).

International Search Report and Written Opinion of the International Searching Authority dated May 16, 2017 for International Application No. PCT/US2017/015584 (11 pages).

International Search Report and Written Opinion of the International Searching Authority dated Jun. 11, 2017 for International Application No. PCT/US2017/019398 (27 Pages).

"Starburst Talon" Specifications Brochure, Angiodynamics, 2013 (2 Pages).

Medtronic, "Aquamantys Bipolar Sealers." Electrosurgical Products, Jun. 2017. Retrieved Jul. 21, 2017 <http://www.medtronic.com/us-en/healthcare-professionals/products/general-surgery/electrosurgical/aquamantys-bipolar-sealers.html> (11 Pages).

"Aquamantys System" Product Brochure, Medtronic, 2014 (12 Pages).

Non-Final Office Action dated Aug. 11, 2017 for U.S. Appl. No. 15/337,334 (11 Pages).

Response to Non-Final Office Action filed Sep. 20, 2017 for U.S. Appl. No. 15/337,334 (6 Pages).

Non-Final Office Action dated Aug. 11, 2017 for U.S. Appl. No. 15/624,327 (11 Pages).

Response to Non-Final Office Action filed Sep. 19, 2017 for U.S. Appl. No. 15/624,327 (8 Pages).

Non-Final Office Action dated Aug. 4, 2017 for U.S. Appl. No. 15/624,230 (18 Pages).

Response to Non-Final Office Action filed Sep. 20, 2017 for U.S. Appl. No. 15/624,230 (10 Pages).

International Search Report and Written Opinion of the International Searching Authority dated Oct. 19, 2017 for International Application No. PCT/US2017/041501 (63 Pages).

International Search Report and Written Opinion of the Interational Searching Authority dated Feb. 27, 2018 for International Application No. PCT/US2017/056754 (11 Pages).

Non-Final Office Action dated May 7, 2018 for U.S. Appl. No. 15/142,616 (13 Pages).

International Search Report and Written Opinion dated Jun. 6, 2018 for International Application No. PCT/US2018/019151 (17 Pages).

Notice of Allowance dated Jul. 24, 2018 for U.S. Appl. No. 15/784,778 (12 Pages).

International Search Report and Written Opinion of the International Searching Authority dated Aug. 26, 2018 for International Application No. PCT/US2017/059850 (10 Pages).

International Search Report and Written Opinion of the International Searching Authority dated Sep. 16, 2018 for International Application No. PCT/US2018/036268 (11 Pages).

International Search Report and Written Opinion of the International Searching Authority dated Nov. 1, 2018 for International Application No. PCT/US2018/043654 (10 Pages).

International Search Report and Written Opinion of the International Searching Authority dated Nov. 15, 2018 for International Application PCT/US2018/043658 (15 Pages).

Extended European Search Report dated Nov. 27, 2018 for European Application No. 16787228.2, (6 pages).

Extended European Search Report dated Jun. 12, 2019, for European Application No. 16860886.7, (8 pages).

Extended European Search Report dated Jul. 16, 2019 for European Application No. 17747970.6 (6 pages).

Official Action dated Jun. 19, 2019 for Japanese Patent Application No. 2018-540040 (11 pages).

Extended European Search Report issued European Patent Application No. 18839274.0, dated Mar. 15, 2021 (9 pages).

Extended European Search Report issued in European Patent Application No. 18839345.8, dated Mar. 12, 2021 (9 pages).

International Search Report and Written Opinion issued in International Application No. PCT/US2018/043658, dated Nov. 15, 2018 (13 pages).

International Search Report and Written Opinion issued in International Application No. PCT/US2020/033357, dated Aug. 27, 2020 (5 pages).

ISA—Search Strategy—Issued by the Israel Patent Office for International Application No. PCT/US2018/043658, dated Nov. 14, 2018 (1 page).

Chinese Office Action and English summary issued in Chinese Application No. 201680062908.2, dated Jun. 30, 2020, 12 pages.

Extended European Search Report issued in European Application No. 18757994.1, dated Nov. 24, 2020, 8 pages.

Extended European Search Report issued in European Patent Application No. 18812643.7, dated Feb. 9, 2021, 7 pages.

Japanese Office Action and English translation issued in Japanese Application No. 2018-521973, dated Nov. 4, 2020, 8 pages.

Extended European Search Report issued in European Application No. 17828289.3, dated Feb. 6, 2020, 5 pages.

Extended European Search Report issued in European Application No. 17895158.8, dated Feb. 28, 2020, 8 pages.

Extended European Search Report issued in European Application No. 19219030.4, dated Jun. 26, 2020, 6 pages.

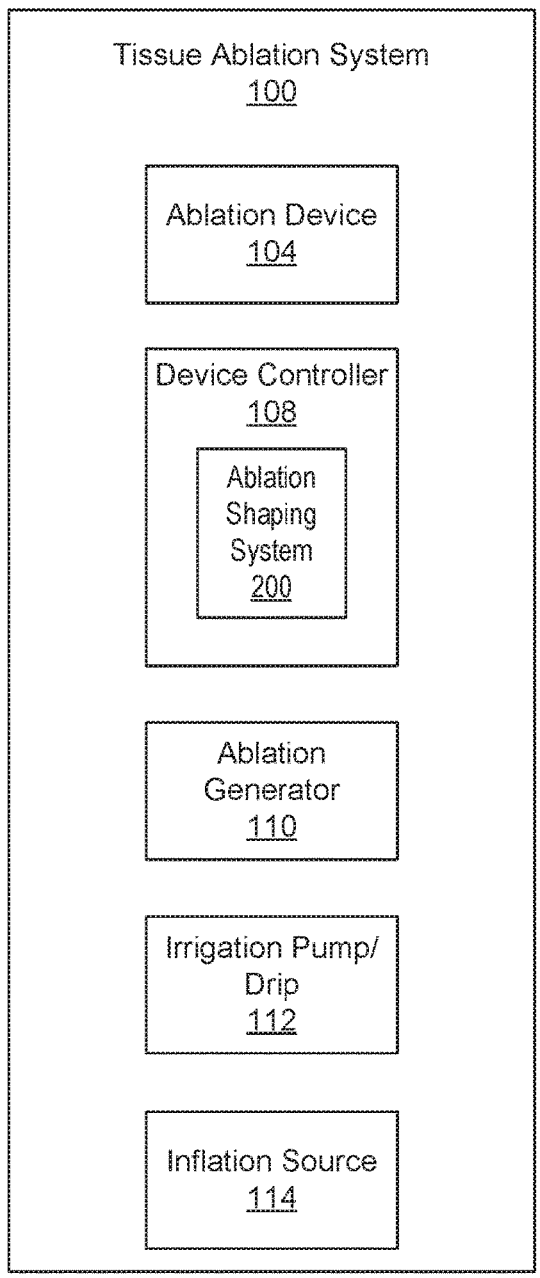
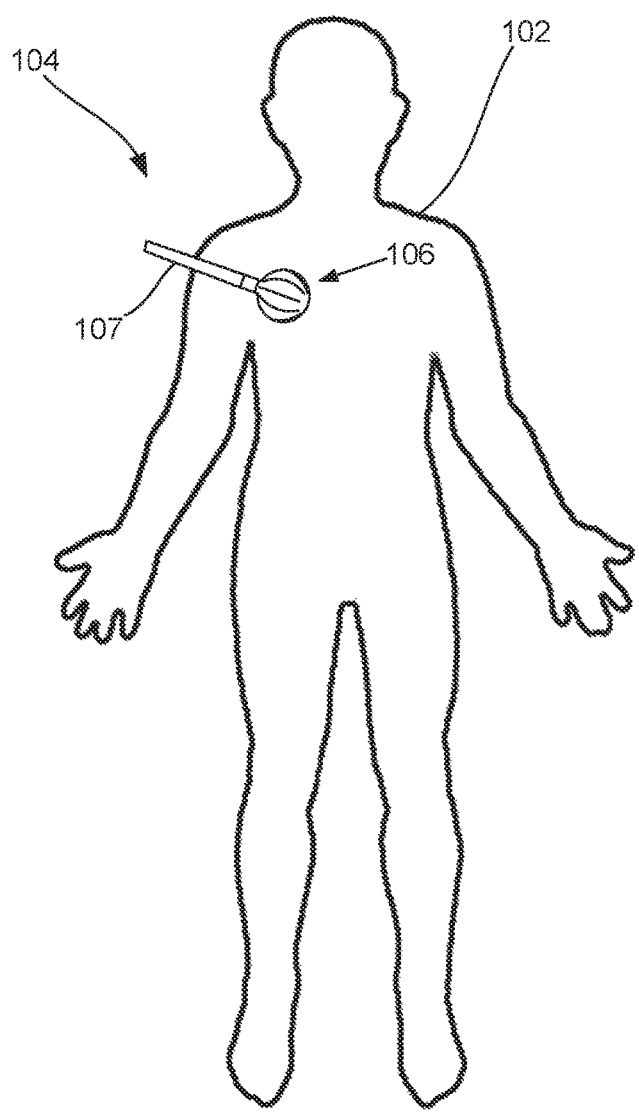
FIG. 2A                    FIG. 2B

TREATMENT DEVICES AND METHODS

CROSS-REFERENCE TO RELATED APPLICATIONS

This application is a continuation of U.S. application Ser. No. 16/122,111, filed Sep. 5, 2018 (and which issued as U.S. Pat. No. 10,470,818 on Nov. 12, 2019), which is a continuation of U.S. application Ser. No. 15/784,778, filed Oct. 16, 2017 (and which issued as U.S. Pat. No. 10,070,921 on Sep. 11, 2018), which claims the benefit of, and priority to, U.S. Provisional Application No. 62/409,103, filed Oct. 17, 2016, the contents of each of which are hereby incorporated by reference herein in their entireties.

FIELD

The present disclosure relates generally to medical devices and methods of treatment with medical devices. In particular, the present disclosure relates to a medical device for ablation of a tissue surface and delivery of a therapeutic that targets diseased cells via a marker whose expression is upregulated by the ablation.

BACKGROUND

Cancer is a group of diseases involving abnormal cell growth with the potential to invade or spread to other parts of the body. Cancer generally manifests into abnormal growths of tissue in the form of a tumor that may be localized to a particular area of a patient's body (e.g., associated with a specific body part or organ) or may be spread throughout. Tumors, both benign and malignant, are commonly treated and removed via surgical intervention, as surgery often offers the greatest chance for complete removal and cure, especially if the cancer has not spread to other parts of the body. However, in some instances, surgery alone is insufficient to adequately remove all cancerous tissue from a local environment.

Some procedures are meant to ablate the marginal tissue and any cancerous cells. For example, surgical removal of a breast tumor (e.g., a lumpectomy) may be accompanied by irradiation. Unlike a mastectomy, a lumpectomy removes only the tumor and a small rim (area) of the normal tissue around it. Radiation therapy is provided in an attempt to kill any cancer cells that may remain. Unfortunately, radiation techniques can be costly, require multiple treatments over several months, and can have devastating side effects on a patient's quality of life. Furthermore, radiation may leave some viable cancer cells in the patient.

SUMMARY

Tumors, both benign and malignant, are commonly treated and destroyed via surgical intervention, as surgery often offers the greatest chance for complete removal and cure, especially if the cancer has not metastasized. However, after the tumor is destroyed, a hollow cavity may remain, wherein tissue surrounding this cavity and surrounding the original tumor site can still leave abnormal or potentially cancerous cells that the surgeon fails, or is unable, to excise. This surrounding tissue is commonly referred to as "margin tissue" or "marginal tissue", and is the location within a patient where a reoccurrence of the tumor may most likely occur.

The device and method described herein can be used during an ablation procedure to destroy a thin rim of normal tissue around the cavity in an effort to manage residual disease in the local environment that has been treated. This technique can help to ensure that all microscopic disease in the local environment has been treated. This is especially true in the treatment of tumors that have a tendency to recur. Applications of such a method of intra-operatively extending tumor margins are applicable to many areas of the body including the liver and especially the breast.

In particular, the present disclosure relates to a medical device and a method of treatment provided by the medical device, wherein the method of treatment, optionally after tissue resection (e.g., tumor resection), includes, by way of the medical device, ablation of a tissue surface or within the resection cavity and delivery of a therapeutic that targets diseased cells (e.g., cancel cells) via a marker whose expression is upregulated by the ablation. The ablation directly kills diseased cells. While some diseased cells evade direct ablation, those cells nevertheless upregulate certain cell surface markers in response to the ablation, even while other, healthy or normal cells do not upregulate expression of the marker in response to the ablation or their upregulation is less than the upregulation of the marker in the diseased cells. Devices and methods disclosed herein are used to deliver a therapeutic that preferentially targets the upregulated cell surface marker to cause the death of those diseased cells. The devices and methods disclosed herein provide a two-prong approach to treating a disease, such as cancer, in which the direct ablation and the therapeutic are linked to each other because the ablation upregulates expression of a target of the therapeutic. Due to this link between the two treatment modalities, cells that manage to escape ablation are preferentially marked for death by the therapeutic.

While primarily discussed in the context of cancel cells of a tissue surface or at tumor margins after resection of a tumor, the skilled artisan will appreciate that the methods and devices described herein are applicable to any diseased or abnormal tissue in which a mechanical stimulus can cause preferential upregulation of cell surface markers of the diseased cells over normal or healthy cells. Similarly, while primarily discussed in the context of breast tissue, the skilled artisan will appreciate that the methods and devices described herein are applicable to any area of the body.

In certain embodiments, ablation and delivery of the therapeutic occur using multiple different devices or multiple different routes of administration. For example, the ablation can occur locally and the therapeutic can be administered systemically. Alternatively, both ablation and therapeutic can be administered locally. The same or different devices can be used to deliver the mechanical stimulus and the therapeutic.

In some embodiments, the method may be performed using an ablation device for providing both the stimulus (i.e., RF ablation) and the therapeutic (i.e., an agent that preferentially targets the target cell type for which expression of the cell surface marker has been upregulated via the stimulus).

According to one aspect, the ablation device of the present invention generally includes a probe including an elongated shaft configured as a handle and adapted for manual manipulation and a nonconductive distal portion coupled to the shaft. The nonconductive distal portion includes an electrode array positioned along an external surface thereof. The distal portion, including the electrode array, can be delivered to and maneuvered within a tissue cavity (e.g., formed from tumor removal) and configured to ablate marginal tissue (via RF energy) immediately surrounding the tissue cavity in order to minimize recurrence of the tumor. The electrode array may be composed of a plurality of conductive members (e.g., conductive wires) electrically isolated and independent from one another. Thus, in some embodiments, each of the plurality of conductive wires, or one or more sets of a combination of conductive wires, is configured to independently receive an electrical current from an energy source (e.g., ablation generator) and independently conduct energy, the energy including RF energy. This allows energy to be selectively delivered to a designated conductive wire or combination of conductive wires. This design also enables the ablation device to function in a bipolar mode because a first conductive wire (or combination of conductive wires) can deliver energy to the surrounding tissue through its electrical connection with an ablation generator while a second conductive wire (or combination of conductive wiress) can function as a ground or neutral conductive member.

In some embodiments, the ablation device is configured to provide RF ablation via a virtual electrode arrangement, which includes distribution of a fluid along an exterior surface of the distal tip and, upon activation of the electrode array, the fluid may carry, or otherwise promote, energy emitted from the electrode array to the surrounding tissue. For example, the nonconductive distal portion of the ablation device includes an interior chamber retaining at least an inner member and a hydrophilic insert surrounding the inner member. The interior chamber of the distal portion is configured to receive and retain a fluid (e.g., saline) therein from a fluid source. The hydrophilic insert is configured receive and evenly distribute the fluid through the distal tip by wicking the saline against gravity through capillary action. The distal portion may generally include a plurality of ports or perforations configured to allow the fluid to pass therethrough, or weep, from the interior chamber to an external surface of the distal portion. The spacer member is shaped and sized so as to maintain the hydrophilic insert in contact with the interior surface of the distal tip wall, and specifically in contact with the one or more ports, such that the hydrophilic insert provides uniformity of saline distribution to the ports. Accordingly, upon positioning the distal portion within a target site (e.g., tissue cavity to be ablated), the electrode array can be activated. The fluid weeping through the ports to the outer surface of the distal portion is able to carry energy from electrode array, thereby creating a virtual electrode. Accordingly, upon the fluid weeping through the perforations, a pool or thin film of fluid is formed on the exterior surface of the distal portion and is configured to ablate surrounding tissue via the RF energy carried from the electrode array.

The therapeutic can be provided in a fluid form (i.e., drug solution) such that the therapeutic can be delivered either concurrently with the saline, or separately, into the interior chamber of the distal tip. In some embodiments, the inner member may be expandable from a collapsed configuration to an expanded configuration (i.e., an expandable balloon). Accordingly, the balloon can be inflated to an expanded configuration, which, in turn, applies a force upon the surrounding hydrophilic insert, thereby forcing the insert against an interior surface of the interior chamber and causing the drug solution to be squeezed out of the hydrophilic insert and through the plurality of ports. This construction ensures a uniform delivery of the drug to the marginal tissue in the resection cavity and also minimizes wastage of the drug, by precisely delivering a controlled dose to the marginal tissue.

In certain embodiments, the target cell type is a cancer cell and the plurality of non-target cell types are non-cancerous cells. The cell surface marker may be a cell surface protein. In some embodiments, the therapeutic comprises an antibody that binds to the cell surface protein. For example, in some embodiments, the ablation kills cancer cells within the marginal tissue and upregulates a marker, such as PD-1, in other cancer cells. The ablation device delivers a therapeutic, such as an anti-PD-1 antibody.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIGS. 2A and 2B are schematic illustrations of an ablation system consistent with the present disclosure:

FIG. 6 illustrates the inner balloon member in a collapsed, or at least partially-collapsed, configuration. FIG. 7 illustrates the inner balloon member in an expanded configuration, which in turn results in application of force upon the surrounding hydrophilic insert to thereby force fluid from the hydrophilic insert through one or more ports and to an exterior surface of the distal portion of the device.

Figure 1:
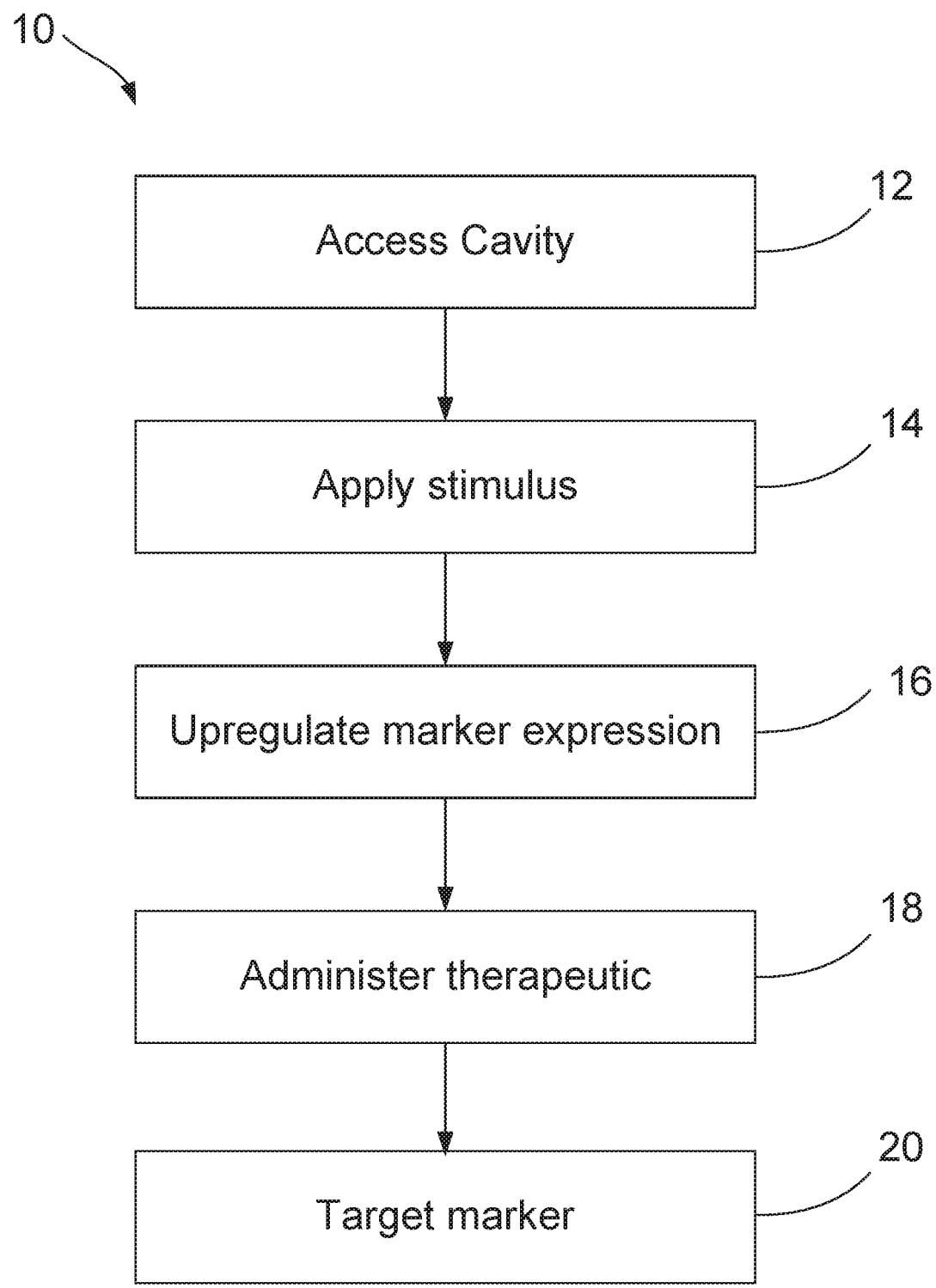
FIG. 1 is a block diagram illustrating a method of treatment consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a medical device and method of treatment using the medical device. In particular, the medical device is configured to apply a stimulus to a target tissue, either on a surface of the tissue, or within a resection cavity, and further deliver a therapeutic that targets diseased cells (e.g., cancel cells) of the target tissue via a marker whose expression is upregulated by the stimulus. The method of treatment may employ a phenomenon by which certain stimuli induce differential expression in cells. For example, RF ablation may cause diseased cells to upregulate expression of certain cell surface proteins at a level not found in healthy or normal cells of the same subject. Accordingly, the medical device may be configured to ablate tissue (ablation is the stimulus) to thereby upregulate expression of a cell surface marker in diseased cells (e.g., cancer cells) of the tissue, and further deliver a therapeutic that targets the diseased cells of the tissue via the cell surface marker.

A tissue ablation system consistent with the present disclosure may be well suited for treating hollow body cavities, such as irregularly-shaped cavities in breast tissue created by a lumpectomy procedure. For example, once a tumor has been removed, a tissue cavity remains. The tissue surrounding this cavity is the location within a patient where a reoccurrence of the tumor may most likely occur. Consequently, after a tumor has been removed, it is desirable to destroy the surrounding tissue (also referred herein as the "margin tissue" or "marginal tissue").

The tissue ablation system of the present disclosure can be used during an ablation procedure to destroy the thin rim of marginal tissue around the cavity in a targeted manner. In particular, the present disclosure is generally directed to a cavitary tissue ablation system including an ablation device to be delivered into a tissue cavity and configured to emit non-ionizing radiation, such as radiofrequency (RF) energy, in a desired shape or pattern so as to deliver treatment for the ablation and destruction of a targeted portion of marginal tissue around the tissue cavity.

In particular embodiments, the method may be performed using an ablation device for providing both the stimulus (i.e., RF ablation) and the therapeutic (i.e., an agent that preferentially targets the target cell type for which expression of the cell surface marker has been upregulated via the stimulus).

The ablation device of the present invention generally includes a probe including an elongated shaft configured as a handle and adapted for manual manipulation and a nonconductive distal portion coupled to the shaft. The nonconductive distal portion includes an electrode array positioned along an external surface thereof. The distal portion, including the electrode array, can be delivered to and maneuvered within a tissue cavity (e.g., formed from tumor removal) and configured to ablate marginal tissue (via RF energy) immediately surrounding the tissue cavity in order to minimize recurrence of the tumor. The electrode array may be composed of a plurality of conductive members (e.g., conductive wires) electrically isolated and independent from one another. Thus, in some embodiments, each of the plurality of conductive wires, or one or more sets of a combination of conductive wires, is configured to independently receive an electrical current from an energy source (e.g., ablation generator) and independently conduct energy, the energy including RF energy. This allows energy to be selectively delivered to a designated conductive wire or combination of conductive wires. This design also enables the ablation device to function in a bipolar mode because a first conductive wire (or combination of conductive wires) can deliver energy to the surrounding tissue through its electrical connection with an ablation generator while a second conductive wire (or combination of conductive wiress) can function as a ground or neutral conductive member.

In some embodiments, the ablation device is configured to provide RF ablation via a virtual electrode arrangement, which includes distribution of a fluid along an exterior surface of the distal tip and, upon activation of the electrode array, the fluid may carry, or otherwise promote, energy emitted from the electrode array to the surrounding tissue. For example, the nonconductive distal portion of the ablation device includes an interior chamber retaining at least an inner member and a hydrophilic insert surrounding the inner member. The interior chamber of the distal portion is configured to receive and retain a fluid (e.g., saline) therein from a fluid source. The hydrophilic insert is configured receive and evenly distribute the fluid through the distal tip by wicking the saline against gravity through capillary action. The distal portion may generally include a plurality of ports or perforations configured to allow the fluid to pass therethrough, or weep, from the interior chamber to an external surface of the distal portion. The spacer member is shaped and sized so as to maintain the hydrophilic insert in contact with the interior surface of the distal tip wall, and specifically in contact with the one or more ports, such that the hydrophilic insert provides uniformity of saline distribution to the ports. Accordingly, upon positioning the distal portion within a target site (e.g., tissue cavity to be ablated), the electrode array can be activated. The fluid weeping through the ports to the outer surface of the distal portion is able to carry energy from electrode array, thereby creating a virtual electrode. Accordingly, upon the fluid weeping through the perforations, a pool or thin film of fluid is formed on the exterior surface of the distal portion and is configured to ablate surrounding tissue via the RF energy carried from the electrode array.

The therapeutic can be provided in a fluid form (i.e., drug solution) such that the therapeutic can be delivered either concurrently with the saline, or separately, into the interior chamber of the distal tip. In some embodiments, the inner member may be expandable from a collapsed configuration to an expanded configuration (i.e., an expandable balloon). Accordingly, the balloon can be inflated to an expanded configuration, which, in turn, applies a force upon the surrounding hydrophilic insert, thereby forcing the insert against an interior surface of the interior chamber and causing the drug solution to be squeezed out of the hydrophilic insert and through the plurality of ports. This construction ensures a uniform delivery of the drug to the marginal tissue in the resection cavity and also minimizes wastage of the drug, by precisely delivering a controlled dose to the marginal tissue.

Accordingly, a tissue ablation device consistent with the present disclosure may be well suited for treating hollow body cavities, such as irregularly-shaped cavities in breast tissue created by a lumpectomy procedure. It should be noted, however, that the devices of the present disclosure are not limited to such post-surgical treatments and, as used herein, the phrase "body cavity" may include non-surgically created cavities, such as natural body cavities and passages, such as the ureter (e.g. for prostate treatment), the uterus (e.g. for uterine ablation or fibroid treatment), fallopian tubes (e.g. for sterilization), and the like. Additionally, or alternatively, tissue ablation devices of the present disclosure may be used for the ablation of marginal tissue in various parts of the body and organs (e.g., skin, lungs, liver, pancreas, etc.) and is not limited to treatment of breast cancer.

FIG. 1 is a block diagram illustrating a method 10 of treatment consistent with the present disclosure. The method 10 includes accessing 12 a cavity from which a tissue mass has been removed. A non-chemical stimulus is mechanically applied 14 within the cavity. The stimulus upregulates 16 expression of a cell surface marker of a target cell type that is within the cavity along with a plurality of non-target cell types. The method 10 includes administering 18 a therapeutic. The therapeutic preferentially targets 20 the target cell type for which expression of the cell surface marker has been upregulated.

In a preferred embodiment, the target cell type is a cancer cell and the plurality of non-target cell types are non-cancerous cells. The cell surface marker is a cell surface protein and the therapeutic comprises an antibody that binds to the cell surface protein. The stimulus includes RF energy and is applied by insertion of a device into the resection cavity. The device may be used to deliver both the stimulus and the therapeutic.

In a specific embodiment, the device is used for RF ablation of marginal tissue within a resection cavity after a lumpectomy. After a breast cancer tumor is removed, the device is inserted into the resulting cavity in the breast. The device is operated to ablate any cancerous cells in the marginal tissue in the cavity. The ablation has a primary effect of directly killing cancerous cells in the marginal tissue. The ablation also has the effect of upregulating expression the PD-1 cell surface protein. It may be found that this effect involves differential expression in that PD-1 expression is upregulated in cancer cells more than in healthy cells. It also may be found that this effect is delocalized in that PD-1 expression is upregulated within the marginal tissue as well is in cells distant from that location. Thus to ensure complete clearance of the breast cancer, after the lumpectomy, not only is the marginal tissue ablated, but an anti-PD-1 therapeutic is administered. Such a treatment method may be performed using a device or system of the disclosure.

FIGS. 2A and 2B are schematic illustrations of an ablation system 100 for providing ablation of a target tissue in a patient 102 to thereby upregulate expression of a cell surface marker and/or protein including enzyme of a target cell type along with a plurality of non-target cell types and for delivering a therapeutic that preferentially targets the target cell type for which expression of the cell surface marker has been upregulated.

The ablation system 100 generally includes an ablation device 104, which includes a probe assembly having a distal tip or portion 106 and an elongated catheter shaft 107 to which the distal tip 106 is connected. The catheter shaft 107 may generally include a nonconductive elongated member including a fluid delivery lumen, in addition to other lumens as described in greater detail herein. The ablation device 104 may further be coupled to a device controller 108 and an ablation generator 110 over an electrical connection (electrical line 124 shown in FIG. 3), an irrigation pump or drip 112 over a fluid connection (fluid line 128 shown in FIG. 3), and an inflation source 114 over a connection (connection line 132 shown in FIG. 3).

As will be described in greater detail herein, the device controller 108 may be used to control the emission of energy from one or more conductive members or wires of the device 104 to result in ablation. In some embodiments, the controller 108 may also be configured to control delivery of fluid to the distal tip 106 so as to control subsequent weeping of fluid from the distal tip 106 during an RF ablation procedure. Yet still, in some cases, the device controller 108 may be configured to control the inflation source 114 the thereby control inflation of an expandable inner balloon member housed within the distal tip 106 to further assist in the weeping of fluid from the distal tip 106, as will be described in greater detail herein.

As will be described in greater detail herein, during an ablation treatment, the ablation generator 110 may generally provide RF energy (e.g., electrical energy in the radiofrequency (RF) range (e.g., 350-800 kHz)) to an electrode array of the ablation device 104, as controlled by the device controller 108. At the same time, saline, and, in some instances, either concurrently or separately, a drug solution including a therapeutic, may also be released from the distal tip 106. The RF energy travels through the blood and tissue of the patient 12 to the return electrode 15 and, in the process, ablates the region(s) of tissues adjacent to portions of the electrode array that have been activated.

The device controller 108 may include hardware/software configured to provide a user with the ability to control electrical output to the ablation device 104 in a manner so as to control ablation output. For example, the ablation device may be configured to operate at least in a "bipolar mode" based on input from a user (e.g., surgeon, clinician, etc.) resulting in the emission of radiofrequency (RF) energy in a bipolar configuration. In some embodiments, the device 104 may be configured to operate in other modes, such as a "measurement mode", in which data can be collected, such as certain measurements (e.g., temperature, conductivity (impedance), etc.) that can be taken and further used by the controller 18 so as to provide an estimation of the state of tissue during a wound treatment procedure. Further still, the device controller 108 may include a custom ablation shaping (CAS) system 200 configured to provide a user with custom ablation shaping, which includes the creation of custom, user-defined ablation geometries or profiles from the device 104. The CAS system 200 may further be configured to provide ablation status mapping and ablation shaping based on real-time data collection (e.g., measurements) collected by the device.

The features and functions of the controller 108 and CAS system 200 are described in at least U.S. Publication No. 2017/0215951 and U.S. Publication No. 2017/0215947, the contents of each of which are incorporated by reference herein in their entireties.

Figure 3:
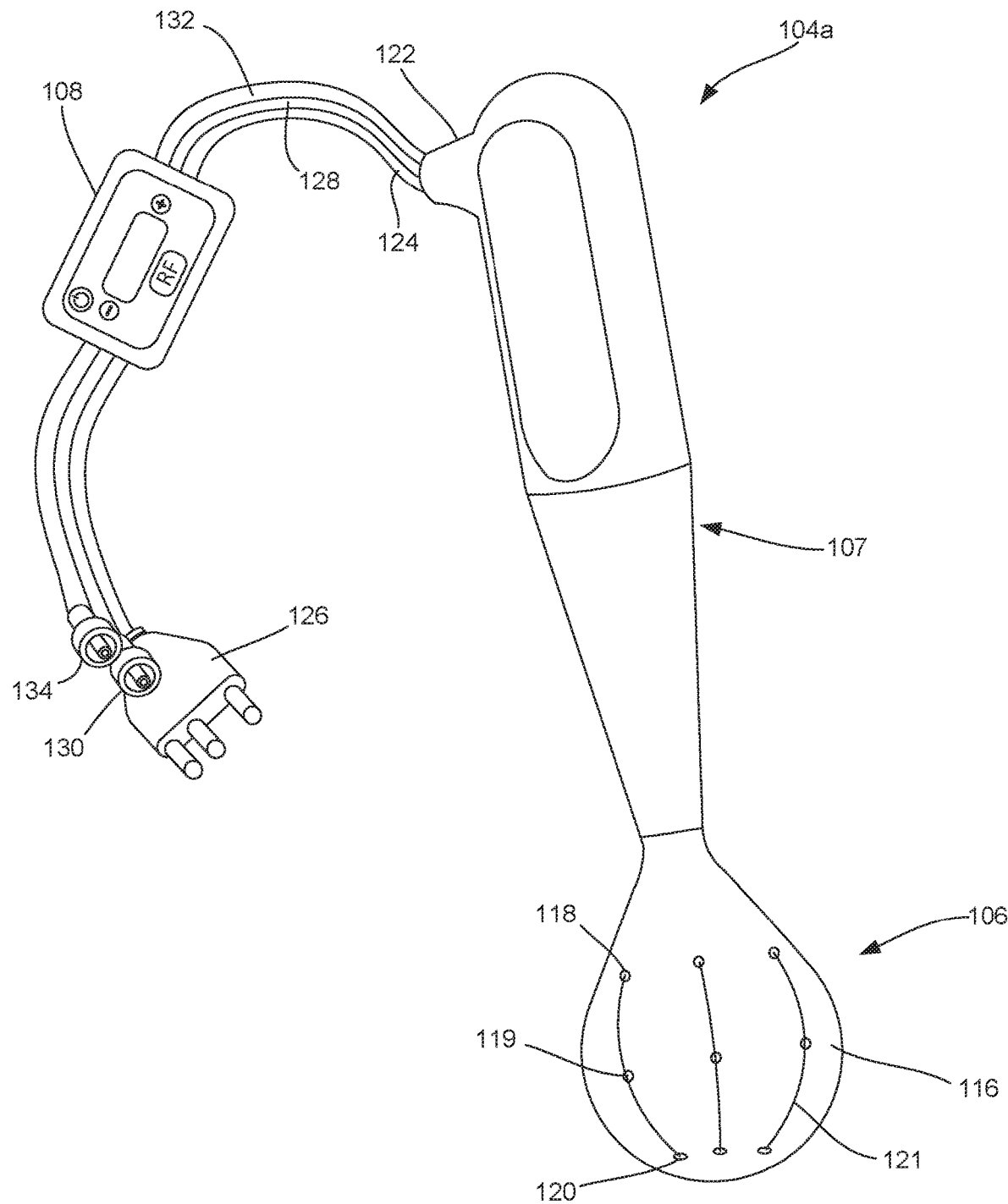
FIG. 3 is a perspective view of one embodiment of an ablation device compatible with the system of FIG. 1A.

FIG. 3 is a perspective view of one embodiment of an ablation device 104a compatible with the system 100 of FIG. 2A. As previously described, the ablation device 104a includes a probe assembly having an elongated shaft 107, which may be configured as a handle and adapted for manual manipulation. Accordingly, as illustrated in FIG. 3, the shaft 107 is in the form of a handle having a distal portion or tip 106 extending therefrom and a proximal end 122. As shown, the proximal end 122 of the device 104a may be coupled to the generator 110, the irrigation pump/drip 112, and the inflation source 114 via connection lines or fittings. For example, the device 104a is coupled to the generator 110 via an electrical line 124, coupled to the irrigation pump/drip 112 via a fluid line 128, and coupled to the inflation source 114 via a connection line 132. Each of the electrical line 124, fluid line 128, and connection line 132 may include an adaptor end 126, 130, 134 configured to couple the associated lines with a respective interface on the generator 110, irrigation pump/drip 112, and inflation source 114.

The distal tip 106 may include a neck portion and a generally spheroid body 116 extending distally from the neck. It should be noted that, in some embodiments, the spheroid body 116 may be generally rigid and may maintain a default shape. However, in some embodiments, the spheroid body 116 may be configured to transition between a collapsed state and an expanded state. For example, the spheroid body 116 may be collapsible to a delivery configuration having a reduced size (e.g., equatorial diameter) relative to the deployed configuration size (e.g., equatorial diameter) of the spheroid body 116.

In some examples, the spheroid body 116 includes a non-conductive material (e.g., a polyamide) as a layer on at least a portion of an internal surface, an external surface, or both an external and internal surface. In other examples, the spheroid body 116 is formed from a non-conductive material. Additionally or alternatively, the spheroid body 116 material can include an elastomeric material or a shape memory material.

In some examples, the spheroid body 116 has a diameter (e.g., an equatorial diameter) of about 80 mm or less. In certain implementations, the spheroid body 116 of the distal tip, in a deployed configuration, has an equatorial diameter of 2.0 mm to 60 mm (e.g., 5 mm, 10 mm, 12 mm, 16 mm, 25 mm, 30 mm, 35 mm, 40 mm, 50 mm, and 60 mm). Based on the surgical procedure, the collapsibility of the spheroid body 26 can enable the distal tip to be delivered using standard sheaths (e.g., an 8F introducer sheath). However, the spheroid body 116 need not be collapsible in some procedures, and thus has a relatively rigid body and maintains the default shape.

The distal tip 116 of the ablation device 14a further includes an electrode array positioned thereon. The electrode array includes at least one conductive member 121. As illustrated, the electrode array may include a plurality of conductive members 121. The plurality of conductive members 121 may extend within the distal tip 106, through one or more ports formed on the spheroid body 116 (i.e., ports 118, 119, 120), and along an external surface of the spheroid body 116. The conductive members 121 extend along the longitudinal length of the distal tip 106 and are radially spaced apart (e.g., equidistantly spaced apart) from each other. These conductive members transmit RF energy from the ablation generator and can be formed of any suitable conductive material (e.g., a metal such as stainless steel, nitinol, or aluminum). In some examples, the conductive members 121 are metal wires. Accordingly, for ease of description, the conductive member(s) will be referred to hereinafter as "conductive wire(s) 121".

As illustrated, one or more of the conductive wires 121 can be electrically isolated from one or more of the remaining conductive wires 121. This electrical isolation enables various operation modes for the ablation device 104a. For example, ablation energy may be supplied to one or more conductive wires 121 in a bipolar mode, a unipolar mode, or a combination bipolar and unipolar mode. In the unipolar mode, ablation energy is delivered between one or more conductive wires 121 on the ablation device 104a. In bipolar mode, energy is delivered between at least two of the conductive wires 121, while at least one conductive wire 121 remains neutral. In other words, at least, one conductive wire functions as a grounded conductive wire (e.g., electrode) by not delivering energy over at least one conductive wire 121.

In some examples, the electrosurgical device 104a may further include a user interface (not shown) serving as the device controller 108 and in electrical communication with at least one of the generator 110, the irrigation pump/drip 112, and/or inflation source 114, and the electrosurgical device 104a. The user interface may include, for example, selectable buttons for providing an operator with one or more operating modes with respect to controlling the energy emission output of the device 104a. For example, selectable buttons may allow a user to control electrical output to the electrosurgical device 104a in a manner so as to control the ablation of a target tissue. Furthermore, in some embodiments, selectable buttons may provide an operator to control the delivery of fluid from the irrigation pump/drip 112 and/or activation of the inflation source 114 to control inflation of an inner balloon member within the distal tip 106 (shown in FIGS. 6 and 7).

As shown in FIG. 3, the spheroid body 116 of the distal tip 106 includes plurality of proximal ports 118, medial ports 119, and distal ports 120 in communication with the at least one lumen of the shaft 107. The proximal ports 118 and distal ports 120 generally serve as openings through which conductive wires 121 of the electrode array may pass. For example, each of the plurality of wires 121 passes through an associated one of the proximal ports and through a corresponding one of the proximal ports. Accordingly, the number of proximal ports 118 and distal ports 120 may generally be equal to the number of conductive wires 121, such that each conductive wire 121 can extend through a different distal port 120, which allows the conductive wires 121 to remain electrically isolated from one another. In other examples, one or more conductive wires can extend through the same distal port 120.

Upon passing through a proximal port 118, each conductive wire 121 can extend along an external surface of the spheroid body 116. In some examples, the length of the conductive wire 121 extending along the external surface is at least 20% (e.g., at least, 50%, 60%, 75%, 85%, 90%, or 99%) of the length of the spheroid body 116. The conductive wire 121 can then re-enter the spheroid body 116 through a corresponding distal port 120. It should be noted, however, that the conductive wires 121 may enter and pass through any number of ports in any particular arrangement, and need not be limited to a single corresponding set of proximal and distal ports.

As shown, one or more of the conductive wires 121 can be electrically isolated from one or more of the remaining conductive wires, such that the electrical isolation enables various operation modes for the electrosurgical device 104a. For example, electrical current may be supplied to one or more conductive wires in a bipolar mode, in which energy is delivered between at least two of the conductive wires, while at least one conductive wire remains neutral. In other words, at least, one conductive wire functions as a grounded conductive wire (e.g., electrode) by not delivering energy over at least one conductive wire.

Since each conductive wire 121 in the electrode array is electrically independent, each conductive wire 121 can be connected in a fashion that allows for impedance measurements using bipolar impedance measurement circuits. For example, the conductive wires can be configured in such a fashion that tetrapolar or guarded tetrapolar electrode configurations can be used. For instance, one pair of conductive wires could function as the current driver and the current return, while another pair of conductive wires could function as a voltage measurement pair. Accordingly, a dispersive ground pad can function as current return and voltage references. Their placement dictate the current paths and thus having multiple references can also benefit by providing additional paths for determining the ablation status of the tissue.

Figure 4:
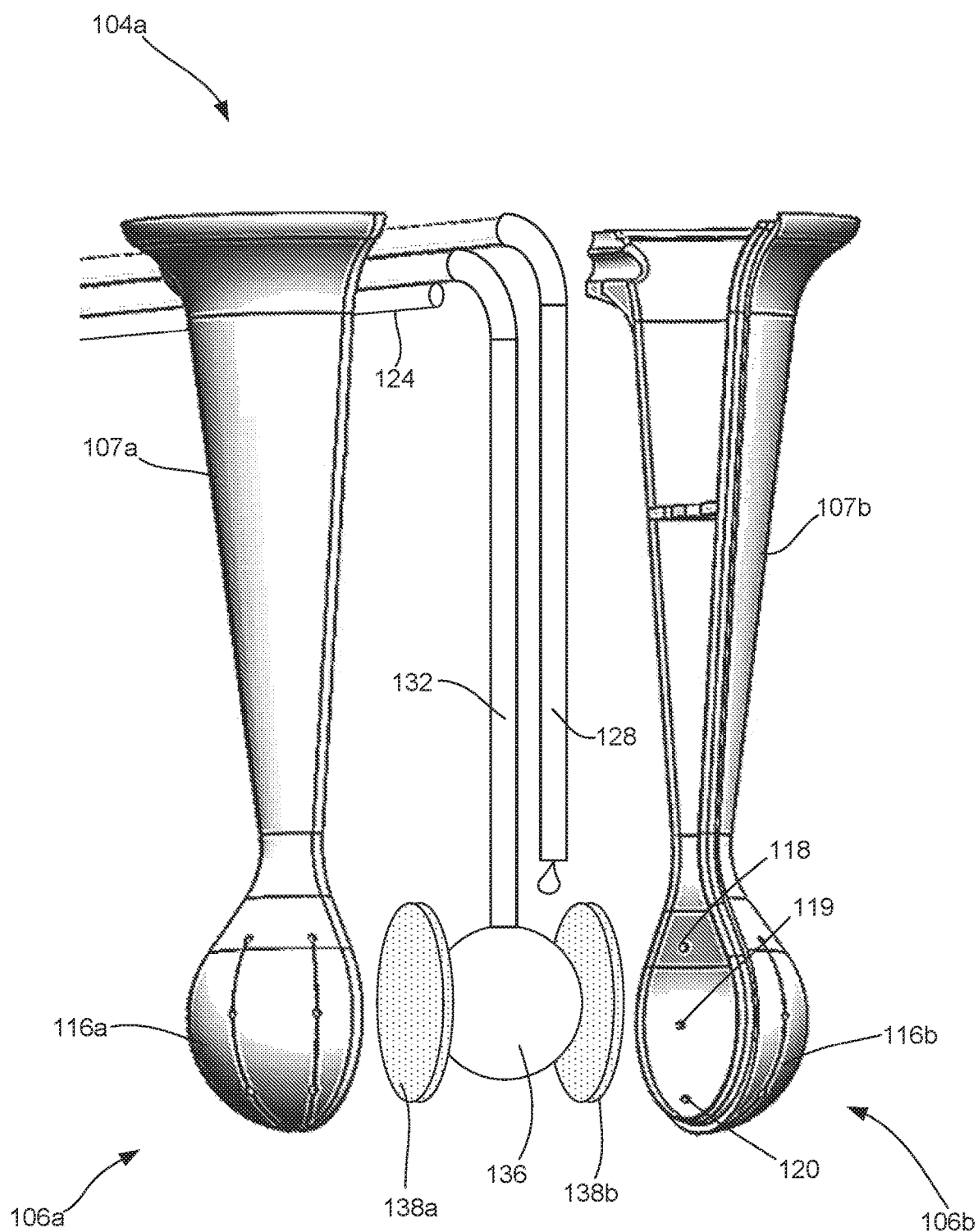
FIG. 4 is an exploded perspective view of the ablation device of FIG. 3.
Figure 5:
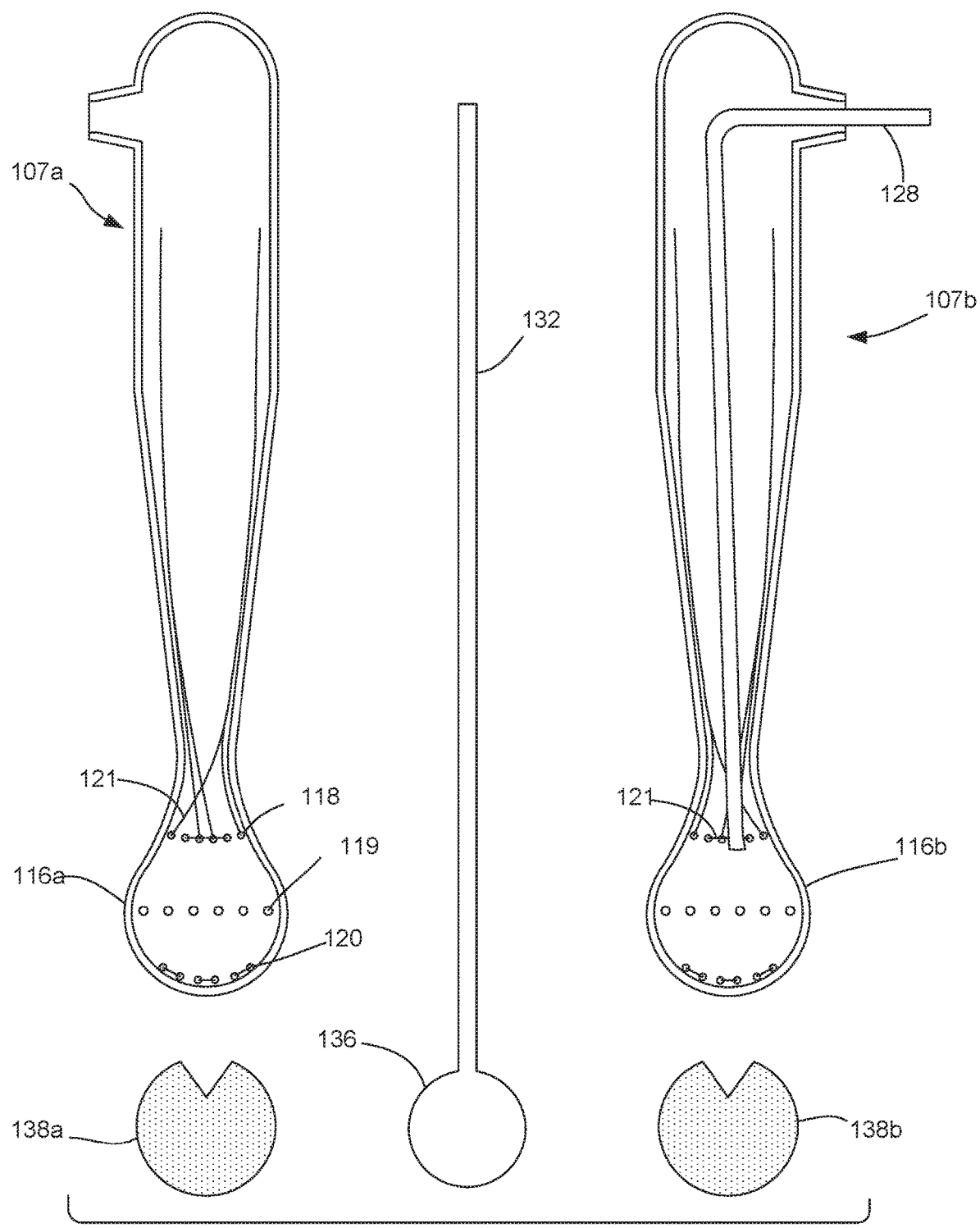
FIG. 5 is a plan view of the ablation device of FIG. 4 illustrating the two halves of the device separated from one another and showing the interior surface of each and internal components.

FIG. 4 is an exploded perspective view of the ablation device 104a and FIG. 5 is a plan view of the ablation device 104a illustrating two halves of the device 104a separated from one another and showing the interior surface of each and internal components. The device 104a includes the distal tip 106 formed from two or more pieces (tip halves 106a and 106b) configured to be coupled to one another to form the unitary distal tip 106. Each half 106a and 106b includes cooperating neck portions and spheroid bodies 116a. 116b, and shafts 107a, 107b. As further illustrated, an electrical line 124 may be provided for coupling the conductive wires 121 to the controller 108 and ablation generator 100, a fluid line 128 may be provided for providing a fluid connection between the irrigation pump/drip 112 and the distal tip 106 so as to provide a conductive fluid (e.g., saline) to the tip 106, and a connection line 132 may be provided for providing a connection between the inflation source 114 and an inflatable member provided within the distal tip 106 (i.e., expandable inner balloon member 136).

As previously described, the ablation device 14 is configured to provide RF ablation via a virtual electrode arrangement. In particular, the device 104a is configured to provide distribution of a fluid along an exterior surface of the distal tip 106 and, upon activation of the electrode array, the fluid may carry, or otherwise promote, energy emitted from the electrode array to the surrounding tissue. For example, a conductive fluid, such as saline, may be provided to the distal tip 106 via the fluid line 128, wherein the saline may be distributed through one or more of the ports (e.g., the proximal ports 118, medial ports 119, and/or distal ports 120). The saline weeping through the ports and to an outer surface of the distal tip 106 is able to carry electrical current from electrode array, such that energy is promoted from the electrode array to the tissue by way of the saline weeping from the ports, thereby creating a virtual electrode. Accordingly, upon the fluid weeping through the ports, a pool or thin film of fluid is formed on the exterior surface of the distal tip 106 and is configured to ablate surrounding tissue via the electrical current carried from the electrode array.

As shown, the nonconductive spheroid body 116 includes an interior chamber (when the first and second halves 116a, 116b are coupled to one another) retaining at least an inner member 136 and one or more hydrophilic inserts 138a, 138b surrounding the inner member 136. The interior chamber of the distal tip 106 is configured to receive and retain a fluid (e.g., saline) therein from a fluid source as well as a drug solution containing the therapeutic, either concurrently or as separate times. The hydrophilic inserts 138a, 138b are configured receive and evenly distribute the fluid throughout the interior chamber of the spheroid body 116 by wicking the saline against gravity. This wicking action improves the uniformity of saline distribution to the ports (e.g., the proximal ports 118, medial ports 119, and/or distal ports 120). The hydrophilic inserts 138a and 138b can be formed from a hydrophilic foam material (e.g., hydrophilic polyurethane).

The inner member 136 may formed from a nonconductive material and may be shaped and sized so as to maintain the hydrophilic inserts 138a. 138b in sufficient contact with the interior surface of the spheroid body 116, and specifically in contact with the one or more ports, such that the hydrophilic inserts 138a, 138b provide uniformity of saline distribution to the ports. In some embodiments, the inner member 136 may have a generally spherical body, corresponding to the interior contour of the chamber of the spheroid body 136.

In some embodiments, the inner member 136 may be expandable from a collapsed configuration to an expanded configuration (i.e., the inner member may be in the form of an expandable balloon). The inner balloon member 136 is in fluid communication with the connection line 132 coupled to the inflation source 114. Accordingly, the inflatable balloon member 136 is in fluid communication with the inflation source 114 via the connection line 132, such that, when the inflation source is activated, the inner balloon member 136 inflates and transitions from a collapsed configuration (shown in FIG. 6) to an expanded configuration (shown in FIG. 7). Upon inflation, the inner balloon member 136 is shaped and sized so as to maintain the hydrophilic insert 138 in contact with the interior surface of the spheroid body 116, and specifically in contact with the one or more ports, such that the hydrophilic insert 137 provides uniformity of saline distribution to the ports. Upon inflating the inner balloon member 136 into the expanded configuration, the inner balloon member applies a force upon the surrounding hydrophilic insert 138, thereby forcing the insert 138 against an interior surface of spheroid body 116 and causing the saline solution and/or drug solution to be squeezed out of the hydrophilic insert 136 and through the plurality of ports. In some embodiments, all of the ports (e.g., proximal ports 118, medial ports 119, and distal ports 129) may be configured to allow for passage of fluid from the inserts 138a. 1388b to the exterior surface of the distal tip 106. However, in some embodiments, only the medial ports 119 may allow for fluid passage, while the proximal and distal ports 118, 120 may be blocked via a heat shrink or other occlusive material.

Figure 6:
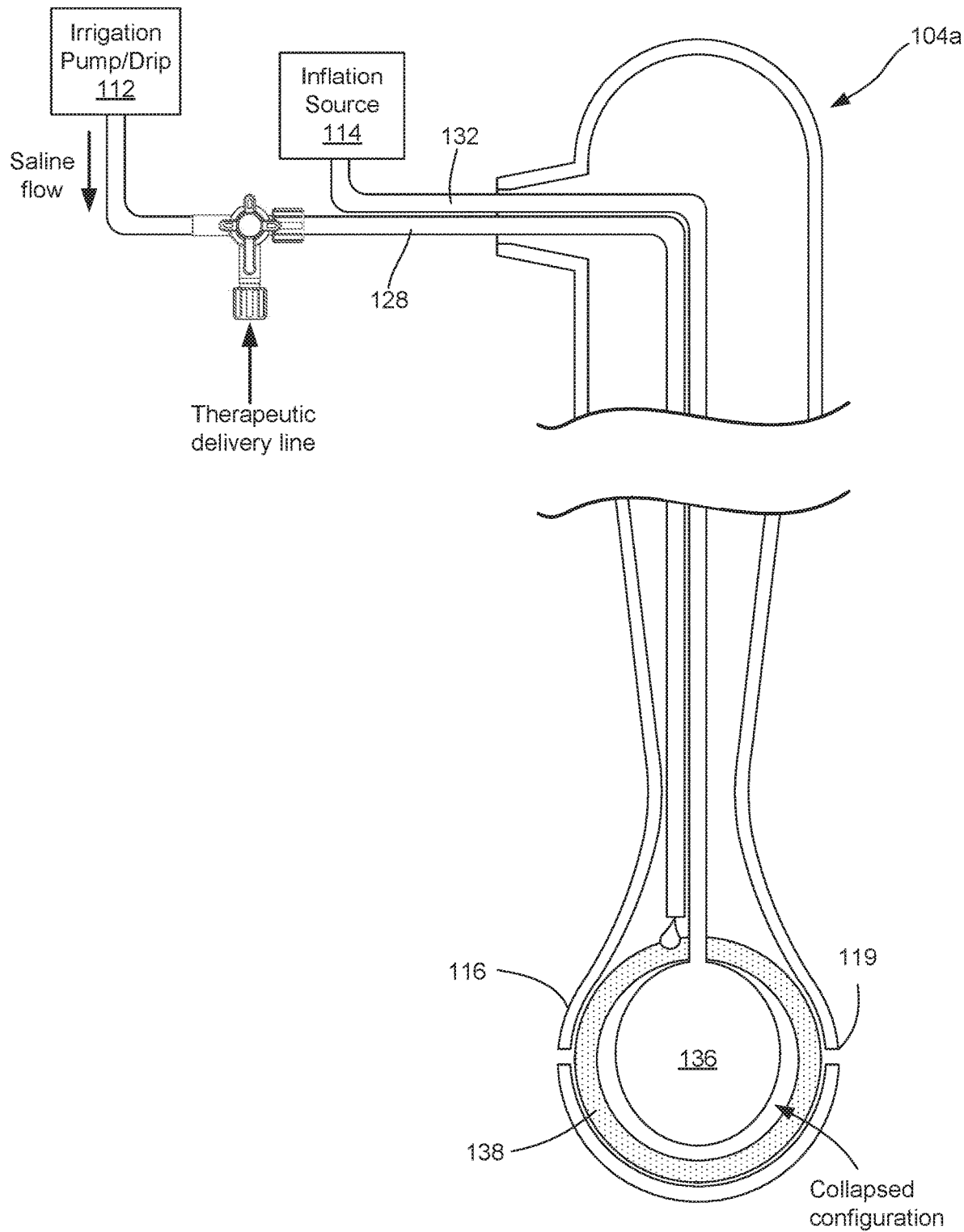
FIGS. 6 and 7 area schematic illustrations of the ablation device of FIG. 3, partly in section, illustrating delivery of fluid from an irrigation pump/drip, which may include a therapeutic, to a hydrophilic insert (foam-like material) within the interior chamber of the distal portion of the device, wherein the fluid can be subsequently distributed to an exterior surface of the distal portion in response to inflation of an inner balloon member to an expanded configuration, thereby resulting in a virtual electrode arrangement upon activation of one or more portions of an electrode array and delivery of the therapeutic to the surrounding tissue.
Figure 7:
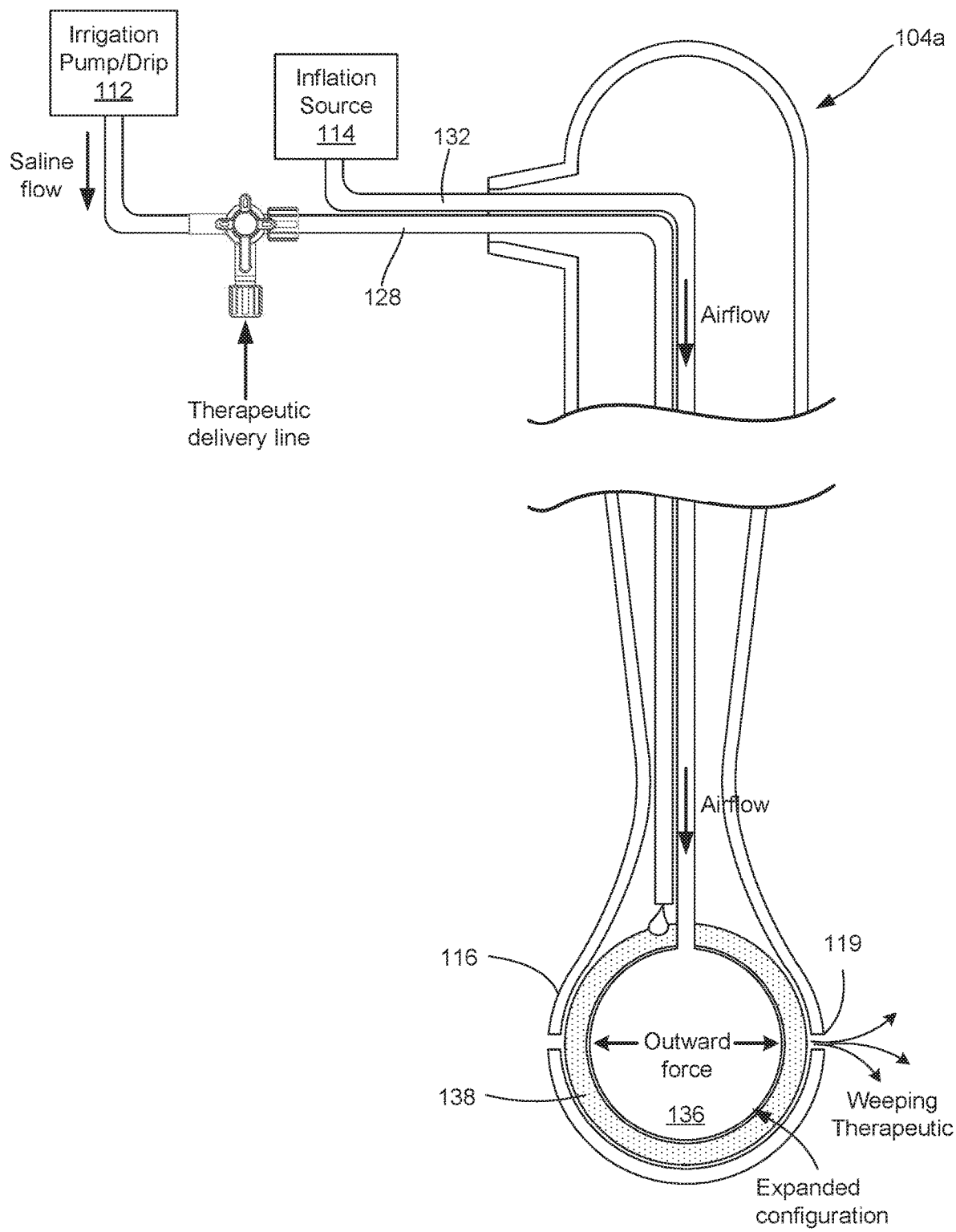

FIGS. 6 and 7 area schematic illustrations of the ablation device of FIG. 3, partly in section, illustrating delivery of fluid from an irrigation pump/drip, which may include a therapeutic, to a hydrophilic insert (foam-like material) within the interior chamber of the distal portion of the device, wherein the fluid can be subsequently distributed to an exterior surface of the distal portion in response to inflation of an inner balloon member to an expanded configuration, thereby resulting in a virtual electrode arrangement upon activation of one or more portions of an electrode array and delivery of the therapeutic to the surrounding tissue. FIG. 6 illustrates the inner balloon member in a collapsed, or at least partially-collapsed, configuration. FIG. 7 illustrates the inner balloon member in an expanded configuration, which in turn results in application of force upon the surrounding hydrophilic insert to thereby force fluid from the hydrophilic insert through one or more ports and to an exterior surface of the distal portion of the device As previously described herein, the therapeutic can be provided in a fluid form (i.e., drug solution) such that the therapeutic can be delivered either concurrently with the saline, or separately, into the interior chamber of the distal tip 106. The arrangement of the inflatable inner balloon member 136 and hydrophilic insert 138 ensures a uniform delivery of the therapeutic to the marginal tissue in the resection cavity and also minimizes wastage of the drug, by precisely delivering a controlled dose to the marginal tissue.

In preferred embodiments, saline is provided for RF ablation and a therapeutic is administered under different conditions. For RF ablation, the saline may be delivered at a pressure that approximates the pressure of the cavity environment. For delivery of the therapeutic, pressure may be increased to aid in delivering the therapeutic into the subject.

Embodiments of the ablation systems and device are provided that include features for the delivery of a therapeutic and mechanical application of a stimulus that causes differential expression of a marker by cell type. Systems and devices can be used in methods that leverage a connection between the differentially expressed marker and the therapeutic to provide effective treatment methods. For example, where the therapeutic attacks cells expressing the marker, and the marker can be differentially expressed in diseased cells, systems and devices are useful for effectively treating the disease. Thus the mechanical systems and devices for delivering a stimulus can include features for delivering the therapeutic.

Any suitable non-chemical stimulus may be provided within the cavity such as RF energy, heat, cryoablation, mechanical ablation, electrocautery, others, or combinations thereof.

The stimulus upregulates expression of a cell surface marker of a target cell type.

Any suitable cell type can be targeted using devices or methods of the disclosure. The target cell type could be, for example, blood cells, bacterial cells, cells of a certain tissue type, cells of a certain genotype or karyotype, cells of a parasite, or cells affected by a medical condition. In preferred embodiments, the target cell type is cancer cells and the non-target cell types are healthy cells in the subject.

Any suitable cell surface markers may be upregulated using the disclosed devices and methods. Suitable markers include, but are not limited to, biomolecules comprising polypeptides, proteins, carbohydrates, lipids, glycoproteins, ribonucleoproteins, lipoproteins, glycolipids and fragments thereof. Typically the marker comprises a membrane protein, including polypeptides, glycoproteins and lipoproteins. Thus the marker may be a transmembrane protein or may be bound to a transmembrane protein or membrane lipid, for example. The marker may be a cell surface receptor. The receptor may comprise a tyrosine kinase receptor, such as an erythropoietin receptor, an insulin receptor, a hormone receptor or a cytokine receptor. Preferred tyrosine kinases include fibroblast growth factor (FGF) receptors, platelet-derived growth factor (PDGF) receptors, nerve growth Factor (NGF) receptors, brain-derived neurotrophic Factor (BDNF) receptors, and neurotrophin-3 (NT-3) receptors, and neurotrophin-4 (NT-4) receptors. The receptor may comprise a guanylyl cyclase receptor such as GC-A & GC-B, a receptor for atrial-natriuretic peptide (ANP) and other natriuretic peptides or GC-C, a guanylin receptor, a member of the ErbB or epidermal growth factor receptor (EGFR) family, e.g. EGFR (ErbB1), HER2 (ErbB2), HER3 (ErbB3), and HER4 (ErbB4), a G protein-coupled receptor (GPCR) such as a muscarinic acetylcholine receptor, an adenosine receptor, an adrenergic receptor, a GABA-B receptor, an angiotensin receptor, a cannabinoid receptor, a cholecystokinin receptor, a dopamine receptor, a glucagon receptor, a histamine receptor, a olfactory receptor, a opioid receptor, a rhodopsin receptor, a secretin receptor, a serotonin receptor or a somatostatin receptor, an ionotropic receptor, for example a nicotinic acetylcholine receptor, a glycine receptor, a GABA-A or GABA-C receptor, a glutamate receptor, an NMDA receptor, an AMPA receptor, a kainate receptor (Glutamate) or a 5-HT3 receptor. The cell surface marker may be a cluster of differentiation antigen, e.g. CD2, CD3, CD4, CD5, CD7, CD8, CD9, CD10, CD11, CD13, CD15, CD16, CD20, CD21, CD22, CD23, CD24, CD25, CD33, CD34, CD36, CD37, CD38, CD41, CD42, CD44, CD45, CD52, CD57, CD60, CD61, CD64, CD71, CD79, CD80, CD95, CD103, CD117, CD122, CD133, CD134, CD138 or CD154.

In one embodiment, the marker is correlated with a disease, preferably a human or animal disease. For example, the marker may be associated with cancer, for example breast or ovarian cancer. Suitable markers may include: CA-125 (MUC-16), CA19-9, HER-2, also known as HER2/neu, erbB-2, EGFR2, ADAM-10, αVββ integrin, Caveolin-1, CD147, CD36, CD63, CD81, Claudin-3, Claudin-4, Desmocollin-1, EGFR, EGFRvIII, EMP-2, EpCAM, ErbB2, GP I b, HLA-DR, Hsp70, Hsp90, MFG-E8, Rab 13, PSA, PSAP, PSMA, Hep Par 1, AFP, CAM 5.2, CD 1 O, Vimentin, RCC, and EMA, Ae 1/3, CAM 5.2, CK19, CEA, PSA, PSAP, PSMA, Thyroglobulin, Calcitonin, HER2, GCDFP-15, Chromogranin, Synaptophysin, CD56, (NCAM), Leu7, CK5/6, CEA, Mucicarmine, B72.3, Leu, M 1, (CD 15), Calretinin, HBME-I, Mesothelin, Vimentin, Mesothelin, 34βE 12, Villin, Uroplakin III, CD 10, CRP, IL6, and PD-1. In preferred embodiments, the cell surface marker is a cell surface protein and the target cell type is in cancer cells.

In certain embodiments, the therapeutic comprises an antibody that binds to the cell surface protein. The cell surface protein is PD-1. The stimulus is applied to ablate tissue within the cavity. Ablation of liver metastases can cause upregulated expression of PD-L1 on primary colorectal tumors. Devices and methods of the disclosure may cause upregulation of PD-L1 in distant tumor cells systemically, especially in lymph nodes and other micro metastasis. In some embodiments. PD-1 inhibitors are used as the therapeutic, e.g., in early breast cancer. For background, see Shi, 2016, PD-1 blockade boosts radiofrequency ablation-elicited adaptive immune responses against tumor. Clin Can Res 22(5): 1173-1184, incorporated by reference.

Use of the disclosed methods and devices provide a variety of benefits. The device 104a can provide both RF ablation and drug delivery. The hydrophilic insert 138 distributes saline uniformly for the RF Ablation, so it should for drug as well. The inner balloon member 136 allows the device to minimize drug waste by effectively squeezing hydrophilic insert 138.

Methods and devices of the disclosure may be beneficial for combination therapy for Triple negative and Her2+ patients who typically have poor outcomes. Methods may increase their response to adjuvant targeted and chemo therapies, and maybe even make it feasible to give immunotherapies to those patients as adjuvant therapy when they first present with cancer.

The disclosure includes a method of treatment that in which ablation has an effect that is synergistic with a therapeutic. In some embodiments, the method includes ablation causing increased concentration of cytokines. Due to the higher levels of cytokines, administration of a therapeutic may result in a greater effect than either ablation or the therapeutic alone. In the preferred embodiments, the ablation causes increased cytokine levels. The method includes mechanically applying, via a device, a non-chemical stimulus within a cavity from which a tissue mass has been removed to thereby causing an increased level of at least one cytokine and administering a therapeutic that has a greater effect in the presence of the at least one cytokine than if the therapeutic were administered alone. Optionally, the therapeutic is administered via the device and the device comprises an elongated probe with a delivery tip at a distal portion of the probe, in which the delivery tip comprises at least one mechanism for application of the stimulus and at least one port for delivery of the therapeutic. Optionally, the elongated probe comprises a catheter with a lumen, the catheter extending along the elongated probe and configured to carry the therapeutic to the delivery tip. Preferably, the at least one mechanism comprises an electrode, and further wherein the device includes a pressure mechanism configured to push the therapeutic out of the at least one port.

Certain embodiments exploit the role of heat shock proteins following radiofrequency ablation. Heat shock protein (HSP) 70 can present tumor antigens to the immune system and induce an immune response against the tumor. HSP70 can prevent apoptosis and protect the tumor cells. Radiofrequency ablation increases the expression of HSP70 in the transition zone of the ablation, with a peak occurring approximately 24 hours after ablation. HSP70 plays a role in this immune response by presenting tumor antigens to dendritic cells. These dendritic cells subsequently present the antigens to CD4+ T-cells, which activate natural killer cells or CD8+ cytotoxic cells to attack the tumor. This response can be enhanced by activating the immune system when the tumor is ablated (using methods such as CTLA-4 antagonists or suppressors of regulatory T-cells).

Clinically, different families of HSPs have been correlated with different behaviors in various types of cancer. In breast cancer, HSP70 overexpression is correlated with poor differentiation, p53 mutation, and a poor prognosis. HSP90 overexpression in breast tumors is also correlated with a poor prognosis. Further, HSP70 overexpression has been shown to indicate resistance to chemotherapy, radiation, and ablation in breast tumors. Evidence suggests HSP70 expression is induced by RFA, specifically in the transition zone. Other markers that may respond to ablation may include CRP and IL6.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A medical device for treating diseased tissue, comprising:
    a fluid line for receiving a therapeutic;
    a rigid spherical body of a fixed diameter defining an interior chamber in fluid communication with the fluid line and configured to receive the therapeutic from the fluid line, the rigid spherical body also defining a plurality of ports configured to allow passage of the therapeutic from the interior chamber to an exterior surface of the rigid spherical body;
    an expandable inner balloon member disposed within the interior chamber of the rigid spherical body, the expandable inner balloon member configured to transition from a collapsed configuration to an expanded configuration;
    a hydrophilic insert disposed within the interior chamber of the rigid spherical body and retained in place between at least a portion of an exterior surface of the expandable inner balloon member and at least a portion of an interior surface of the rigid spherical body, the hydrophilic insert configured to receive and distribute the therapeutic to at least some of the plurality of ports; and
    a plurality of conductive wires wherein each of the plurality of wires includes a portion disposed along at least a portion of the exterior surface of the rigid spherical body.

2. The medical device of claim 1, wherein each of the plurality of wires is configured to receive an electrical current and conduct energy.

3. The medical device of claim 2, wherein the therapeutic is active against cells having a marker that is upregulated by ablation.

4. The medical device of claim 3, wherein the therapeutic comprises an antibody.

5. The medical device of claim 4, wherein the marker is PD-1 and the therapeutic comprises an anti-PD-1 antibody.

6. The medical device of claim 2, further comprising a mechanism for controlling transitioning of the expandable inner balloon member between the collapsed configuration, the expanded configuration and a plurality of configurations therebetween.

7. The medical device of claim 6, wherein the mechanism is operable to inflate the expandable inner balloon member to a first diameter during an ablation procedure and to a second, larger diameter for delivery of the therapeutic.

8. The medical device of claim 7, wherein, when the expandable inner balloon member is inflated to the second, larger diameter, the expandable inner balloon member applies a force upon the hydrophilic insert sufficient to cause the hydrophilic insert to be compressed between at least a portion of the exterior surface of the expandable inner balloon member and at least a portion of the interior surface of the rigid spherical body and to further expel the therapeutic from the hydrophilic insert and through at least one of the plurality of ports.

9. The medical device of claim 2, wherein the device is operable for simultaneous ablation and delivery of the therapeutic through one or more of the plurality of ports.

10. The medical device of claim 2, wherein each of the plurality of wires is configured to conduct radiofrequency (RF) energy upon receipt of the electrical current.

11. The medical device of claim 1, wherein the therapeutic is distributed within the hydrophilic insert.

12. The medical device of claim 11, wherein the therapeutic is active against cells having a protein including an enzyme that is upregulated by the ablation.

13. The medical device of claim 12, wherein the enzyme is thymidine phosphorylase.

14. The medical device of claim 1, wherein the plurality of ports comprises a plurality of proximal ports and distal ports, wherein each of the plurality of wires passes through at least one of the proximal ports and through a corresponding one of the distal ports, wherein each of the plurality of proximal ports corresponds to a separate one of the plurality of distal ports such that a portion of the conductive wire passing through a set of corresponding proximal and distal ports has a length that extends along the exterior surface of the rigid spherical body between the corresponding proximal and distal ports.

15. The medical device of claim 14, wherein the conductive wire extends along at least 20% of a length of the exterior surface of the rigid spherical body.

16. The medical device of claim 14, wherein each of the plurality of conductive wires passes through a different distal port.

17. The medical device of claim 14, wherein each of the plurality of conductive wires passes through a different proximal port.

18. The medical device of claim 1, wherein the plurality of ports comprises one or more medial ports on the rigid spherical body and is configured to allow passage of the therapeutic from the interior chamber of the rigid spherical body to the exterior surface of the rigid spherical body.

* * * * *